(12) United States Patent
Alden et al.

(10) Patent No.: US 7,246,319 B2
(45) Date of Patent: Jul. 17, 2007

(54) INFORMATION SYSTEM SUPPORTING CUSTOMIZABLE USER INTERFACES AND PROCESS FLOWS

(75) Inventors: Rhett Alden, Seattle, WA (US); Patrick Yamaura, Bellevue, WA (US); Robert Munger, Seattle, WA (US)

(73) Assignee: IDX Systems Corporation, Burlington, VT (US)

( * ) Notice: Subject to any disclaimer, the term of this patent is extended or adjusted under 35 U.S.C. 154(b) by 352 days.

(21) Appl. No.: 10/923,604

(22) Filed: Aug. 20, 2004

(65) Prior Publication Data

US 2005/0057436 A1    Mar. 17, 2005

Related U.S. Application Data

(60) Provisional application No. 60/497,141, filed on Aug. 22, 2003.

(51) Int. Cl.
*G06F 13/00* (2006.01)
*G06F 15/00* (2006.01)

(52) U.S. Cl. ............... 715/738; 715/737; 715/744; 709/204

(58) Field of Classification Search ............... 715/513, 715/764, 765, 763, 853, 854, 736, 744, 738, 715/737; 709/204, 205
See application file for complete search history.

(56) References Cited

U.S. PATENT DOCUMENTS 7,051,071 B2 * 5/2006 Stewart et al. ............... 709/204

2003/0145283 A1 * 7/2003 Machida et al. ............ 715/513
2003/0171947 A1 * 9/2003 Ledford et al. .............. 705/1

OTHER PUBLICATIONS

Microsoft, "Airborne Express, Smart Client Solution Helps Airborne Express Decrease Call Center Costs and Build Stronger Customer Connections," [online] [Retrieved from the Internet Jan. 24, 2005], Posted: May 23, 2003, URL<http://www.microsoft.com/resources/casestudies/CaseStudy.asp?CaseStudyID=14067>, pp. 1-11.
Microsoft, "Thomson Financial, Investment Management Group Extends Technology With Smart Client and Web Services," [online] [Retrieved from the Internet Jan. 24, 2005], Posted: Jun. 9, 2003, URL<http://www.microsoft.com/resources/casestudies/CaseStudy.asp?CaseStudyID=14085>, pp. 1-8.

(Continued)

*Primary Examiner*—Cao (Kevin) Nguyen
(74) *Attorney, Agent, or Firm*—Andrus, Sceales, Starke & Sawall, LLP (57) ABSTRACT

An information system engages in a communications session with a client to process a workflow. A context object stores information describing the session. Transfer objects store data utilized to process the workflow. A client action causes the information system to provide the transfer objects to a workflow engine. The workflow engine processes actions in the workflow utilizing the transfer objects. The information system selects among multiple screen definitions for the client based in part on the context. A transformation module filters the data in the transfer objects to isolate the data that are utilized by the screen definition. The screen definition and filtered data are provided to the client.

28 Claims, 9 Drawing Sheets

OTHER PUBLICATIONS

Microsoft, "Smart Clients in Business: Expanding the Edges of the Enterprise Network," White Paper, [online] [Retrieved from the Internet Jan. 24, 2005], Published Mar. 26, 2004, URL<http://download.microsoft.com/download/f/3/7/f3771bbb-b1fd-4f5d-8af6-a5a5a6c9d3dc/SmartClientsWhitePaper.doc>, pp. 1-10.

Richter, Jeffrey, Microsoft, msdn magazine, "Microsoft.NET Framework Delivers the Platform for an Integrated, Service-Oriented Web," [online] [Retrieved from the Internet Jan. 24, 2005], Published Sep. 2000, URL<http://msdn.microsoft.com/library/default.asp?url=/msdnmag/issues/0900/framework/toc.asp>, pp. 1-11.

Richter, Jeffrey, Microsoft, msdn magazine, "Part 2: Microsoft .NET Framework Delivers the Platform for an Integrated, Service-Oriented Web," [online] [Retrieved from the Internet Jan. 24, 2005], Published Oct. 2000, URL<http://msdn.microsoft.com/library/default.asp?url=/msdnmag/issues/1000/framework2/toc.Asp?frame=true>, pp. 1-11.

* cited by examiner

INFORMATION SYSTEM SUPPORTING CUSTOMIZABLE USER INTERFACES AND PROCESS FLOWS

CROSS-REFERENCE TO RELATED APPLICATION

This application claims the benefit of U.S. Provisional Application No. 60/497,141, filed Aug. 22, 2003, which is hereby incorporated by reference herein.

BACKGROUND OF THE INVENTION

1. Field of the Invention

This invention pertains in general to a user interface for a computerized information system. In particular, this invention pertains to a user interface that is highly-customizable.

2. Description of the Related Art

An information system (IS) is used by an enterprise to process and share data. For example, a hospital or other health care organization uses a hospital information system (HIS) to manage data utilized in the day-to-day operation of the hospital. The data can relate to clinical events, patients, orders, scheduling, billing, insurance, etc. The HIS is utilized by various people, including clinicians, such as doctors and nurses, and administrators, such as billing specialists, to perform their respective roles at the hospital.

Different enterprises often prefer to utilize different workflows with respect to the IS. For example, a first hospital might require a patient to provide next-of-kin information upon admission, while a second hospital might not collect kin information at that time. The enterprises would like the user interfaces presented by the IS to track the enterprises' workflows. Thus, the enterprise that collects kin information during admission would prefer that the admissions user interface have a field for entering next-of-kin information, or at least link to another user interface where the information can be provided.

Similarly, end-users in different roles often prefer different process flows and associated user interfaces. For example, a doctor treating a patient in an emergency room might need to see different information than a doctor treating a patient in an outpatient setting. Likewise, a nurse administering medicine might need to see different patient information than a doctor who is ordering a prescription. In another example, a given user might prefer that a user interface is in a particular language.

However, the information systems do not provide this degree of flexibility with respect to workflows or interfaces. The information systems often have a hardcoded workflow, where every interaction with the system traverses through a fixed set of user interfaces, and every user interface collects a fixed set of information. Therefore, significant engineering effort is required to customize the system for different enterprises and/or end-users. This problem is especially acute for vendors of information systems that may need or want to customize the system for many different enterprises and users.

Thus, there is a need in the art for a way to easily customize workflows and user-interfaces for information systems.

BRIEF SUMMARY OF THE INVENTION

The above need is met by an IS in which the visual representation of a workflow at the client is decoupled from the processing of the workflow. This decoupling allows the visual representation and/or workflow to be customized for particular clients, end-users, enterprises, etc.

In one embodiment, the IS engages in a communications session with a client to process a workflow. A context module maintains a context object for the session. The context object stores information describing the session including, for example, the current point in the workflow, the type of client device, and/or end-user preferences.

In one embodiment, the IS stores data utilized to process the workflow in a representation called a "transfer object." A workflow engine processes actions at the current point in the workflow and may act on the data in a transfer object. In response to the processing, the IS selects among multiple screen definitions based in part on the context. A screen definition defines a user interface to present at a client and, in one embodiment, specifies data that are utilized by the user interface. A transformation module filters the data in the transfer object and/or from other sources in the IS to isolate only the data that are utilized by the user interface defined by the selected screen definition. The IS provides the screen definition and filtered data to the client.

The figures depict an embodiment of the present invention for purposes of illustration only. One skilled in the art will readily recognize from the following description that alternative embodiments of the structures and methods illustrated herein may be employed without departing from the principles of the invention described herein.

DETAILED DESCRIPTION OF THE PREFERRED EMBODIMENTS

Figure 1:
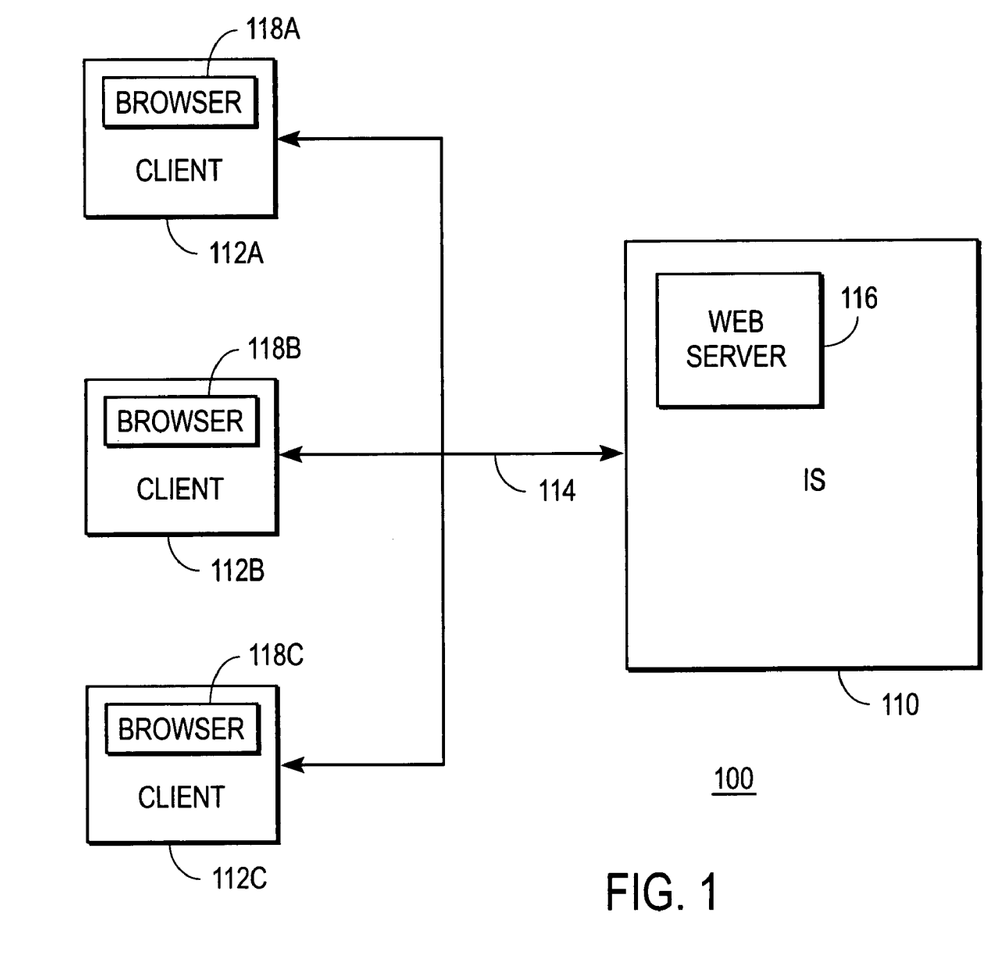
FIG. 1 is a high-level block diagram illustrating an environment utilizing an embodiment of the present invention.

FIG. 1 is a high-level block diagram illustrating an environment 100 utilizing an embodiment of the present invention. In the figures, like elements are identified with like reference numerals. A letter after the reference numeral, such as "112A," indicates that the text refers specifically to the element having that particular reference numeral. A reference numeral in the text without a following letter, such as "112," refers to any or all of the elements in the figures bearing that reference number (e.g. "112" in the text refers to reference numerals "112A" and/or "112B" in the figures).

The illustrated environment 100 includes an information system (IS) 110 in communication with three clients 112 via a network 114. In one embodiment, the IS 110 and clients 112 are associated with an enterprise. As used herein, an "enterprise" is a business, governmental entity, nonprofit organization, or other entity having one or more geographic locations or facilities.

In one embodiment, the enterprise is a healthcare enterprise composed of one or more hospitals, clinics, or other healthcare organizations and the IS 110 is a healthcare information system (HIS). For this reason, the present description uses explanations and examples drawn from healthcare settings in order to explain the operation of the IS 110. However, in other embodiments the enterprise is not related to healthcare. For example, the enterprise can be a financial institution, government office, communications company, etc.

The IS 110 stores information utilized by the enterprise. If the enterprise is a healthcare enterprise, the IS 110 stores clinical data, patient demographic data, billing data, etc. that are used by the staff of the hospital. If the enterprise is a financial institution, the IS 110 stores account balances, financial transactions, customer addresses, and other elements pertinent to the financial enterprise. In one embodiment, the IS 110 executes a web server 116 that communicates with the clients 112.

In general, the clients 112 are electronic devices that allow end-users to view information held within the IS 110 and provide information to the IS, although a client may also be another enterprise's IS. A client 112 can be, for example, a personal computer system, a portable digital assistant (PDA), a cellular telephone, or a pager. Although only three clients 112 are shown in FIG. 1, embodiments of the present invention can have many different clients interacting with the IS 110.

In one embodiment, the client 112 executes a web browser 118 such as INTERNET EXPLORER from Microsoft Corp. of Redmond, Wash. The web browser 118 communicates with the web server 116 within the IS 110. In one embodiment, the web browser 118 downloads information from the web server 116 that the browser uses to instantiate a portal on a display device associated with the client 112. The portal can instantiate user interface (UI) elements (e.g., list boxes) and populate the elements with information. An end-user uses the UI elements to interact with the IS 110.

In one embodiment, the web server 116 and web browser 118 utilize the .NET Framework available from Microsoft Corp. to create and execute the portal. In another embodiment, the web server 116 and web browser 118 utilize other technologies, such as JAVA available from Sun Microsystems, Inc. of Santa Clara, Calif. In one embodiment, the web browser 118 is integrated into the client 112 and/or into other software at the client, such as the operating system.

The network 114 allows the electronic exchange of data between the IS 110 and the clients 112. In one embodiment, the network is a private network operated by the enterprise. In another embodiment, the network is the Internet and may include both public and private links. In one embodiment, the network 116 uses standard communications technologies and/or protocols. Thus, the network 116 can include links using technologies such as Ethernet, 802.11, integrated services digital network (ISDN), digital subscriber line (DSL), asynchronous transfer mode (ATM), etc. Similarly, the networking protocols used on the network 116 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), etc. The data exchanged over the network 116 can be represented using technologies and/or formats including the hypertext markup language (HTML), the extensible markup language (XML), etc. In addition, all or some of links can be encrypted using conventional encryption technologies such as the secure sockets layer (SSL), Secure HTTP and/or virtual private networks (VPNs). In another embodiment, the entities can use custom and/or dedicated data communications technologies instead of, or in addition to, the ones described above.

Figure 2:
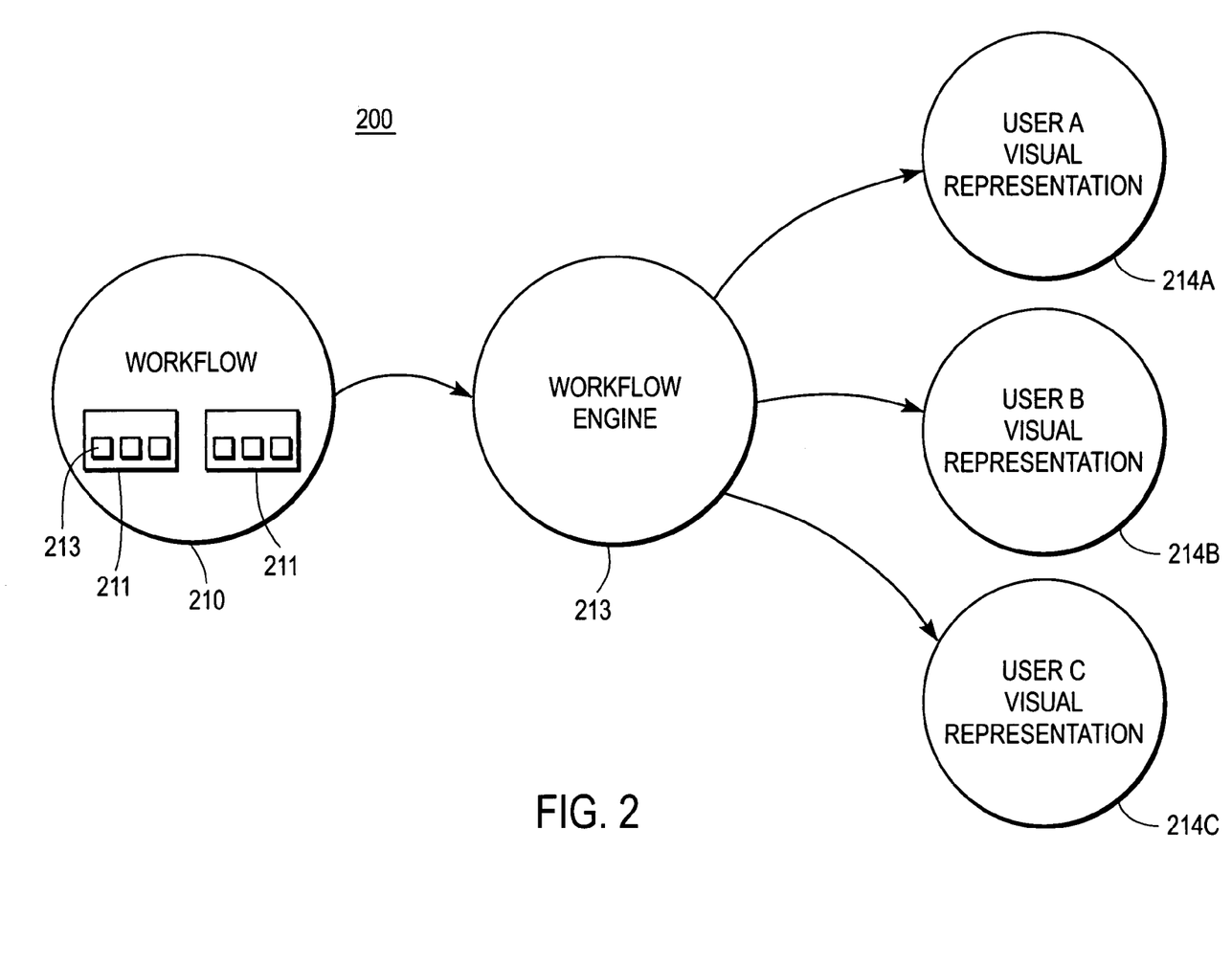
FIG. 2 illustrates a high-level conceptual view of how an end-user interacts with an information system according to an embodiment of the present invention.

FIG. 2 illustrates a high-level conceptual view of how an end-user interacts with the IS 110 according to an embodiment of the present invention. End-users use the clients 112 to interact with the IS 110 and perform work. Work is defined in terms of a workflow 210. A workflow 210, in turn, is defined in terms of one or more activities 211. Examples of activities include admitting a patient to a hospital, placing an order for a prescription drug, creating a new account for a bank customer, and transferring funds between accounts.

An activity 211 is formed from a set of actions 213. For example, the activity of establishing a new bank account might include the action of inputting the social security number of the person owning the account. Likewise, the activity of ordering a drug might include the action of selecting the drug from among a list of drugs. In one embodiment, a workflow engine 213 executes the workflow 210. As part of this function, the workflow engine 213 evaluates decision logic and chooses branches or paths in the flow based on data in the IS 110, data received from the client 112 and/or data from other sources.

The visual representation 214 of the workflow 210 executed by the workflow engine 213 is comprised of display screens. Each display screen includes UI elements that the end-user can utilize to interact with the IS 210 while performing the workflow. In one embodiment, actions 213 in the workflow 210 can be bound to UI elements in a display screen. For example, an action requiring the end-user to provide a name can be bound to a list box that lists possible names. Likewise, the same action can be bound to a text box that the end-user uses to type the name.

The IS 110 in one embodiment allows multiple visual representations 214 to be associated with a particular point in a workflow 210. Each visual representation 214 provides UI elements that allow an end-user to perform the actions 213 within the workflow 210, but the UI elements need not be the same on each visual representation 214. In addition, the visual representations 214 need not include or display the same information. Thus, even if end-user A and end-user B are at the same point in the same workflow, they can have receive different visual representations 214 of that workflow 210. In more concrete terms, the IS 110 can present a doctor and a nurse each performing the same workflow with different visual representations 214 representing the same point in the workflow 210. Similarly in another embodiment, the IS 110 can present a doctor performing a workflow 210 using a different client device, such as a PDA, with a different visual representation 214 than the visual representation provided to a doctor performing the workflow using a PC.

The workflow 210 is thus decoupled from the visual representation of the workflow 214. This decoupling allows the workflow 210 to be defined and/or altered independently from the visual representation of the workflow 214. Moreover, this decoupling allows the visual representation for a workflow 214 to be customized for particular end-users, roles of end-users, languages, enterprises, etc. As a result, one can use the same information system 110 to support the different workflows and visual representations that may be required by different parts of the enterprises.

Figure 3:
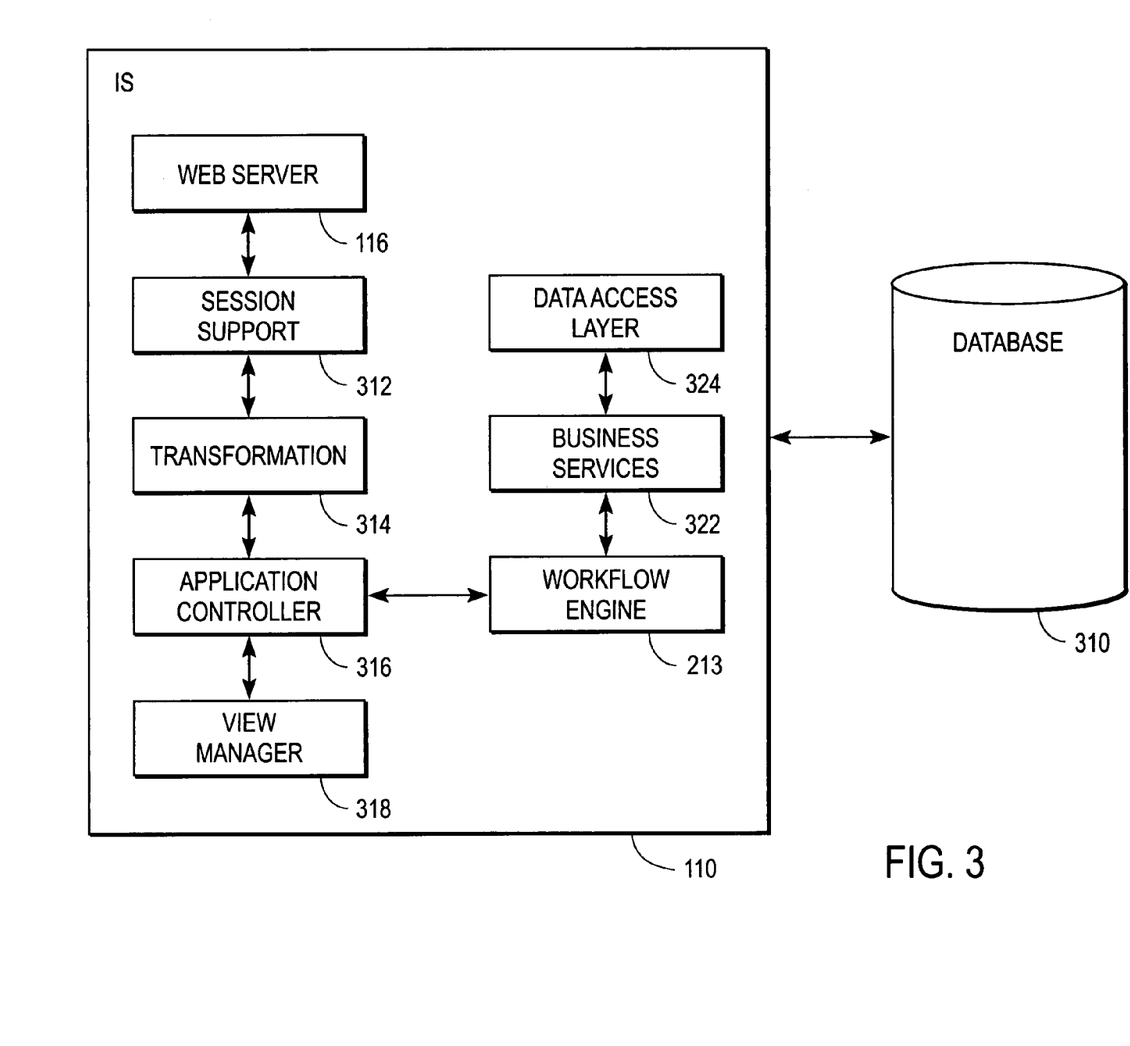
FIG. 3 is a high-level block diagram illustrating a more detailed view of the information system according to one embodiment.

FIG. 3 is a high-level block diagram illustrating a more detailed view of the IS 110 according to one embodiment. In one embodiment, the IS 110 executes on a conventional computer system having one or more processors such as an INTEL x86 or POWERPC-compatible central processing units (CPUs), a memory, a network adapter, and one or more persistent storage devices. The specific types of hardware and software within the computer system may vary depending upon the implementation of the IS 110. For example, an IS 110 operating in a high-volume environment may have multiple processors and hard drive subsystems in order to provide a high processing throughput. In addition, the IS 110 can include hardware and software for providing fault-tolerant operation and guaranteed availability.

In one embodiment, program modules for providing the functionality attributed to the IS 110 are stored on a storage device, loaded into the memory, and executed by a processor. Alternatively, hardware or software modules may be stored elsewhere within the IS 110. As used herein, the term "module" refers to computer program logic and/or data for providing the specified functionality. A module can be implemented in hardware, firmware, and/or software. Embodiments of the IS 110 and other entities described herein can include other and/or different modules than the ones described here. In addition, the functionality attributed to the modules can be performed by other or different modules in other embodiments. Moreover, this description occasionally omits the term "module" for purposes of clarity and convenience. For example, this description often refers to the web server module 116 as the "web server."

In FIG. 3, the arrows between the modules represent a flow of information through the IS 110 in one embodiment, but do not necessarily represent physical and/or logical connections between the modules. In addition, information can flow through the system (e.g., from module to module) in ways other than those illustrated in FIG. 3 and/or described herein.

FIG. 3 illustrates that the IS 110 is in communication with a database 310. In general, the database 310 stores information utilized by the IS 10. As used herein, the term "database" refers to an information store and does not imply that the data within the "database" is organized in a particular structure beyond that described herein. Although only a single database 310 is illustrated in FIG. 3, embodiments of the IS 310 can utilize multiple databases. In addition, a database 310 can be local to the IS 110 (e.g., on a persistent storage within the computer operating the IS) or remote to the IS (e.g. the database can be connected to the IS via the network 114). The database 310 is illustrated as being separate from the IS 110 for purposes of clarity although this is not necessarily the case.

The IS 110 of FIG. 3 includes the web server 116. In one embodiment, the web server 116 communicates with the web browser 118 in the client 112 and exchanges XML-encoded messages using the HTTP. Other embodiments utilize other encodings for the messages. In one embodiment, the communications between the web server 116 and browser 118 are stateless, meaning that each message is self-contained and interpreted independently from other messages.

In one embodiment, messages sent from the web server 116 to the browser 118 include information such as the types of UI elements to instantiate in the portal at the client 112, and information to include within the UI elements. For example, an XML message from the web server 116 to the browser 118 can instruct the browser to instantiate a list box UI element and populate the list box with a set of names.

In one embodiment, messages sent from the web browser 118 to the web server 116 include information indicating the actions of an end-user of the client 112. In one embodiment, these actions include selecting a UI element and/or selecting data displayed by a UI element. For example, an XML message from the browser 118 to the web server 116 can indicate that the end-user clicked an "OK" button displayed by the UI and/or selected a particular name from a list box.

A session support module 312 within the IS 110 exchanges data between the web server 116 and a transformation module 314 and provides data transformation facilities and functionality utilized to support communications with multiple clients 112. A set of related communications between a client 112 and the IS 110 is referred to as a "session." For example, an end-user who logs into the IS 110 in order to process a workflow is engaged in a session.

Figure 4:
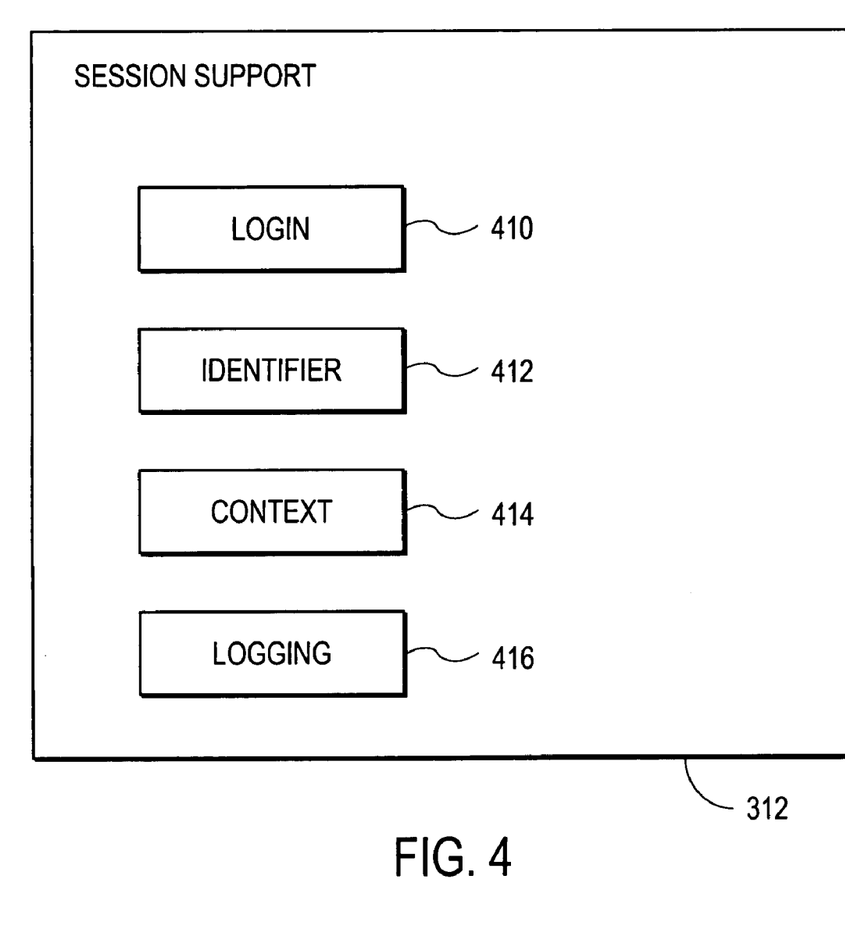
FIG. 4 is a high-level block diagram illustrating functional modules within the session support module according to one embodiment.

FIG. 4 is a high-level block diagram illustrating functional modules within the session support module 312 according to one embodiment. A login module 410 allows an end-user of a client 112 to log into the IS 110 and establish a session. For example, the end-user can provide a login/password pair that the session support module 312 utilizes to authenticate and authorize the end-user. Likewise, the login module 410 terminates sessions when appropriate.

In one embodiment, an identifier module 412 establishes a unique identifier (e.g., a cookie in one embodiment) used by the client 112 to identify the session. In one embodiment, the identifier module 412 also establishes a unique identifier at the client that uniquely identifies the client and/or end-user. Communications from the client 112 to the IS 110 include one or both of the identifiers, and allow the session support module 312 to uniquely identify the sessions to which messages belong and/or the clients 112 and/or the end-users that sent the messages.

In one embodiment, a context module 414 maintains context information for the multiple sessions that may exist at any given time. Since communications between the browser 118 and web server 116 are stateless, the context module 414 uses the unique identifiers received from the client 112 to maintain and retrieve context from a persistence store for each session. The context module 414 updates and serializes the context for each session when appropriate. In one embodiment, the context module 414 updates the context for a session each time it encounters a message belonging to that session.

In one embodiment, the context information indicates the current point in the workflow for the session. The context information can also include a user profile that holds preferences and/or settings for the given end-user, such as the end-user's role, preferred language, etc. The context information can also include a device profile for the specific device being utilized as the client 112. In one embodiment, the context information is stored in the database 310.

In one embodiment, the context module 414 holds the context information for a session in an object-oriented representation called a "context object." This context object is passed to the various modules in the IS 110 that require access to the context information.

In one embodiment, a logging module 416 logs events that occur on the IS 110. The logged events include messages received from and/or sent to the clients 112, actions performed by the workflow engine 213, etc. The logs are used to audit use of the IS 110 as may be necessary or desired. In one embodiment, these logs are used to audit usage for compliance with government healthcare regulatory guidelines.

Returning now to FIG. 3, the transformation module 314 communicates with the session support module 312 and an application controller module 316. The transformation module 314 acts as a filter or interface between the data displayed at a client 112 as part of a visual representation of a workflow and the data stored and/or utilized in the IS 110 in processing a workflow.

Figure 5:
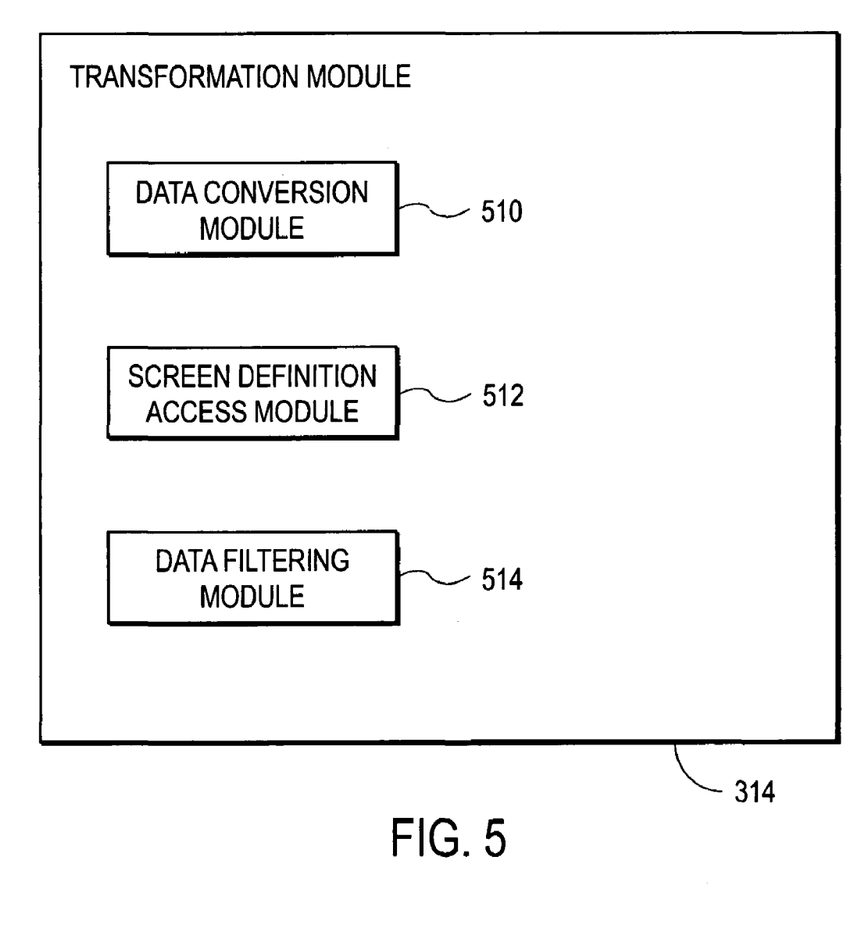
FIG. 5 is a high-level block diagram illustrating functional modules within the transformation module according to one embodiment.

FIG. 5 is a high-level block diagram illustrating functional modules within the transformation module 314 according to one embodiment. A data conversion module 510 converts messages between the metadata representation, which uses XML in one embodiment, utilized to communicate with clients 112 and the internal representations utilized by the IS 110. In one embodiment, the internal representation utilized by the IS 110 is a "transfer object." A transfer object is an object of a given class that stores data pertinent to that class. For example, in one embodiment a "patient" transfer object contains data about a patient and an "order" transfer object contains information about an order placed by a clinician.

A screen definition access module 512 utilizes a reference to a screen definition to retrieve a screen definition from the database 310. This reference is called a "screen name." A screen definition specifies a UI to be instantiated at a client 112 for a given screen (i.e., for a given visual representation 214 of a workflow). To this end, the screen definition specifies the controls and/or other UI elements to appear on the screen and also specifies positional information for the UI elements. The screen definition also specifies the data types to bind to the UI elements. In one embodiment, the data types are specified using XML and correspond to the schema used in the XML messages exchanged between the IS 110 and the client 112. For example, a given screen definition can specify that a screen has a list control in the center of the screen, that the list displays n rows simultaneously, and that each row of the list displays a patient name, diagnosis, and assigned physician.

A data filtering module 514 filters data based on the screen definition retrieved by the screen definition access module 512 to isolate only data utilized by UI elements on the screen. In one embodiment, a transfer object received from another module in the IS 110 will include more data than is utilized by UI elements on a given screen. The data filtering module 512 filters out information that is not utilized on the screen defined by the screen definition. In one embodiment, the filtered data is utilized by the data conversion module to form an XML message for a client 112.

For example, assume a data transfer object for a patient contains both the patient's date of birth and social security number. However, the UI element in the applicable screen definition displays only the patient's date of birth. The data filtering module 514 filters out the patient's social security number. When the data conversion module 510 converts the transfer object into a XML message, the message contains only the patient's date of birth and not the social security number.

Returning now to FIG. 3, the application controller module 316 communicates with the transformation module 314, a view manager 318, and the work flow engine 213 in one embodiment. The application controller 316 functions as a mediator for the IS 110. Said another way, the application controller 316 serves as the contact point between the executed workflow 210 and the visual representation of the workflow 214.

In one embodiment, the application controller 316 passes data transfer and context objects from the transformation module 314 to the workflow engine 213. In one embodiment, the application controller 316 also receives data transfer and context objects from the workflow engine 213 and passes them to the transformation module 314. In response to receiving a context object from the workflow engine 213, the application controller 316 provides the context object to the view manager 318 in order to obtain a screen name for the given context.

The view manager module 318 determines the appropriate screen to display at a client 112 at a given point in a workflow. In one embodiment, the view manager 318 receives a context object and analyzes it to determine the appropriate screen. The context object will indicate, for example, the ID of the end-user, the ID and/or type of device being utilized as a client 112, the active language, and the point within the workflow associated with the session. The view manager 318 accesses a set of screen names in the database 310 and identifies the applicable screen name. In one embodiment, the view manager 318 adds the screen name 318 to the context object.

The workflow engine module 213 controls the execution of the workflow for the IS 110. In one embodiment, the workflow engine 213 receives transfer and context objects from the application controller 316, identifies the applicable workflow, executes the appropriate activities in the workflow, and outputs the results of the execution as part of the context. In one embodiment, the output takes the form of new and/or modified transfer and/or context objects which are provided back to the application controller 316.

Figure 6:
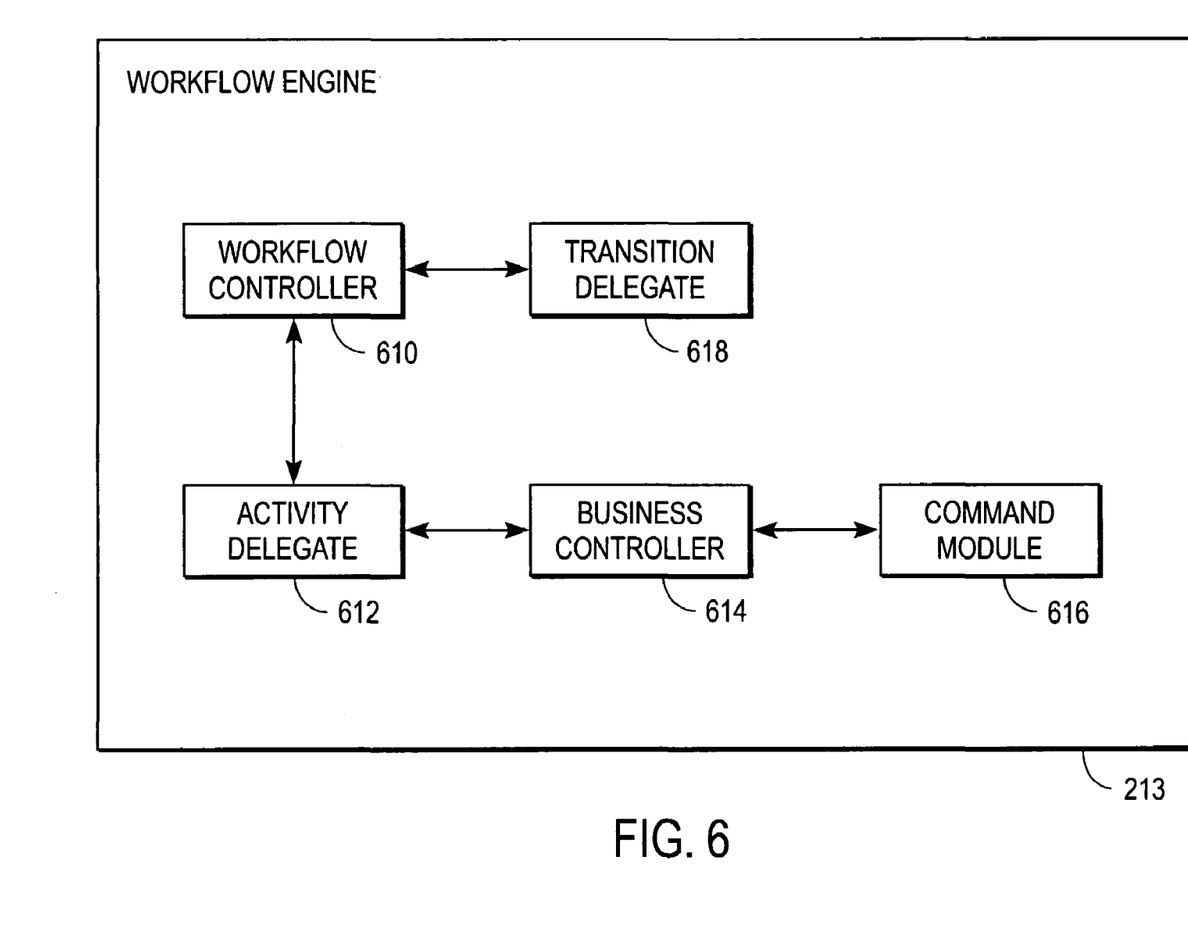
FIG. 6 is a high-level block diagram illustrating functional modules within the workflow engine according to one embodiment.

FIG. 6 is a high-level block diagram illustrating functional modules within the workflow engine 213 according to one embodiment. A workflow controller module 610 identifies the appropriate workflow based on the context. In one embodiment, the workflow controller 610 accesses a set of possible workflows stored in the database 310 and uses the workflow information in the context to select the applicable workflow. The applicable workflow becomes part of the context and is provided to the other modules within the workflow engine 213.

In one embodiment, an activity delegate module 612 receives the transfer and context objects. The activity delegate 612 analyzes the workflow in view of the context and identifies the one or more activities within the workflow that are ready to be performed. In one embodiment, the activity delegate 612 adds the identified activities to the context.

In one embodiment, a business controller module 614 receives the transfer and context objects. The business controller 614 identifies the one or more actions within an identified activity in the workflow that are ready to be performed. In addition, the business controller 614 identifies one or more commands that will perform the actions. The business controller 614 invokes the commands using the relevant data from the transfer and/or context objects as parameters, and thereby performs the appropriate actions of the workflow. For example, in one embodiment the action to be performed is retrieving patient information based on a patient selected from a list box. To perform this action, the business controller 614 invokes a command called "Get Patient Information" and passes an identifier of the patient as a parameter.

In one embodiment, a command module 616 receives a command invocation and any associated parameters from the business controller module 614. The command module 616 identifies specific business services performed by the business services module 322 (shown in FIG. 3) that correspond to the command invocation and calls those business services with the appropriate parameters. The command module 616 thus provides a layer of indirection between the workflow engine 213 and the business services module 322. This layer allows the business controller 614 to reference activities using different identifiers than those used by the business services module 322.

In one embodiment, a transition delegate module 618 evaluates results of workflow actions invoked by the business controller 614 and identifies the next activity and/or action to perform in the workflow. In one embodiment, the workflow has branching paths. The transition delegate 618 selects the applicable branch based on the results of an activity or action. For example, assume the action performed by the business controller 614 is a "save record" command. If the save command completes successfully, the transition delegate 618 selects a branch of the workflow that presents a "Save Successful" UI message to the end-user. If the save operation fails, the transition delegate 618 selects a branch of the workflow that presents a "Save Failed" UI message to the end-user.

Returning now to FIG. 3, the IS 110 includes a business services module 322 in communication with the workflow engine 213. In one embodiment, the business services module 322 includes the business knowledge utilized to execute the commands of the workflows performed by the IS 110. The functionality of the business services module 322 is thus adapted to the particular environment in which the IS is used.

In one embodiment, the business services module 322 executes a set of discrete functions for performing the business logic. For example, if the IS 110 is utilized in a healthcare environment, the business services module 322 performs functions for tasks like searching a patient database for duplicate patients, checking a patient's record for potentially harmful drug interactions, etc. In another example, if the IS 110 is utilized in a financial institution environment, the business services module 322 performs functions for tasks like determining account balances, transferring funds, buying securities, etc. In one embodiment, the business services module 322 receives a transfer object as a parameter and also returns a transfer object as its output after performing the appropriate functions.

A data access layer module 324 acts as an interface between modules of the IS 110 and the database 310. The data access layer 324 serves as an abstraction between the object-oriented representations of the transfer and/or context objects and the database-specific representations of the data. To this end, the data access layer 324 maintains relationships between the objects (and data within the objects) and specific fields within the database 310.

In one embodiment, the data access layer module 324 receives requests from the other modules of the IS 110 for access to information stored in the database 310. Such requests can include read and write requests. In response, the data access layer 324 generates and executes the appropriate database query or queries to access the data within the database 310. In the case of a read request, the data access layer creates an object having the data read from the database 310 (or adds the data to an existing object). In one embodiment, only the business services module 322 accesses the database 310 through the data access layer 324. Other modules within the IS 110 access the database 310 directly, or utilize separate databases for their respective data.

Figure 7:
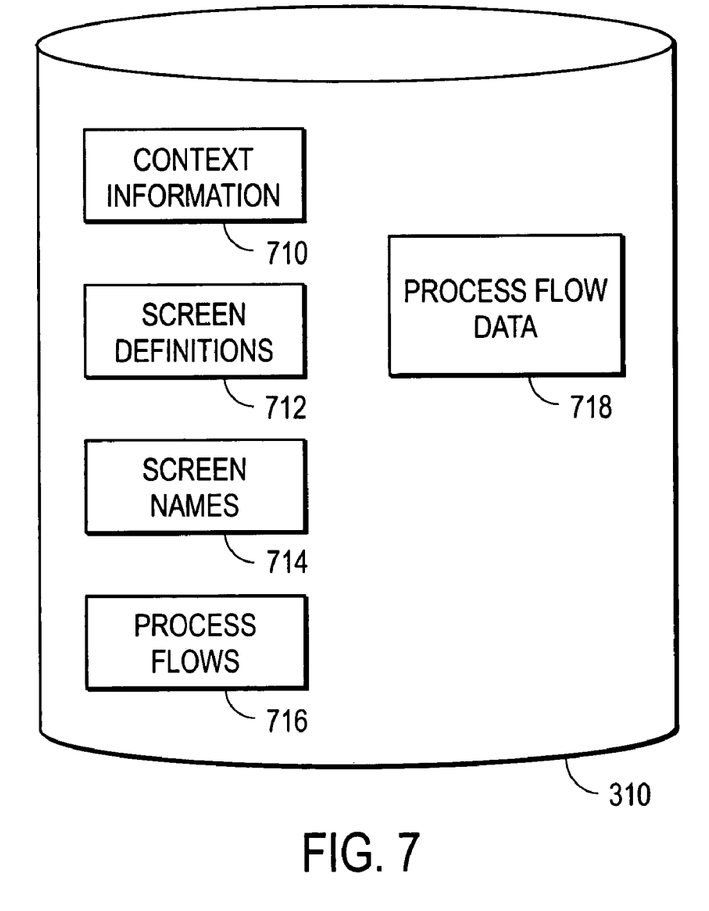
FIG. 7 is a high-level block diagram illustrating data modules within the database according to one embodiment.

FIG. 7 is a high-level block diagram illustrating data modules within the database 310 according to one embodiment. As described above, embodiments of the IS 110 can utilize multiple databases. The modules illustrated in FIG. 7 represent data stored within the one or more databases in one embodiment. In other embodiments, the one or more databases can store different data modules in addition to, or instead of, the modules illustrated in FIG. 7.

In the illustrated embodiment, the database 310 includes a context information module 710 for storing context information. As described above, in one embodiment the context information indicates the current point in the workflow for a given client 112 and/or end user, and also includes profiles for given end-users and/or clients 112.

The database 310 also includes a screen definitions module 712 for holding screen definitions utilized by the IS 110 and a screen names module 714 for holding screen names. The screen names in the screen names module 714 are references to the screen definitions in the screen definitions module 712. In one embodiment, there is a one-to-one mapping between screen names and screen definitions. That is, each screen name has an associated screen definition. Other embodiments include many-to-one or other types of mappings.

In one embodiment, the database 310 includes a workflows module 716 for storing the workflows implemented by the IS 110. In one embodiment, the workflows are represented using an XML schema, although other embodiments utilize other representations. The database 310 also includes a workflow data module 718 for storing information utilized during the course of executing the workflows. The workflow data module 718 stores, for example, the data contained within the transfer objects (patient names, etc.) and utilized by the modules within the IS 110.

Figure 8:
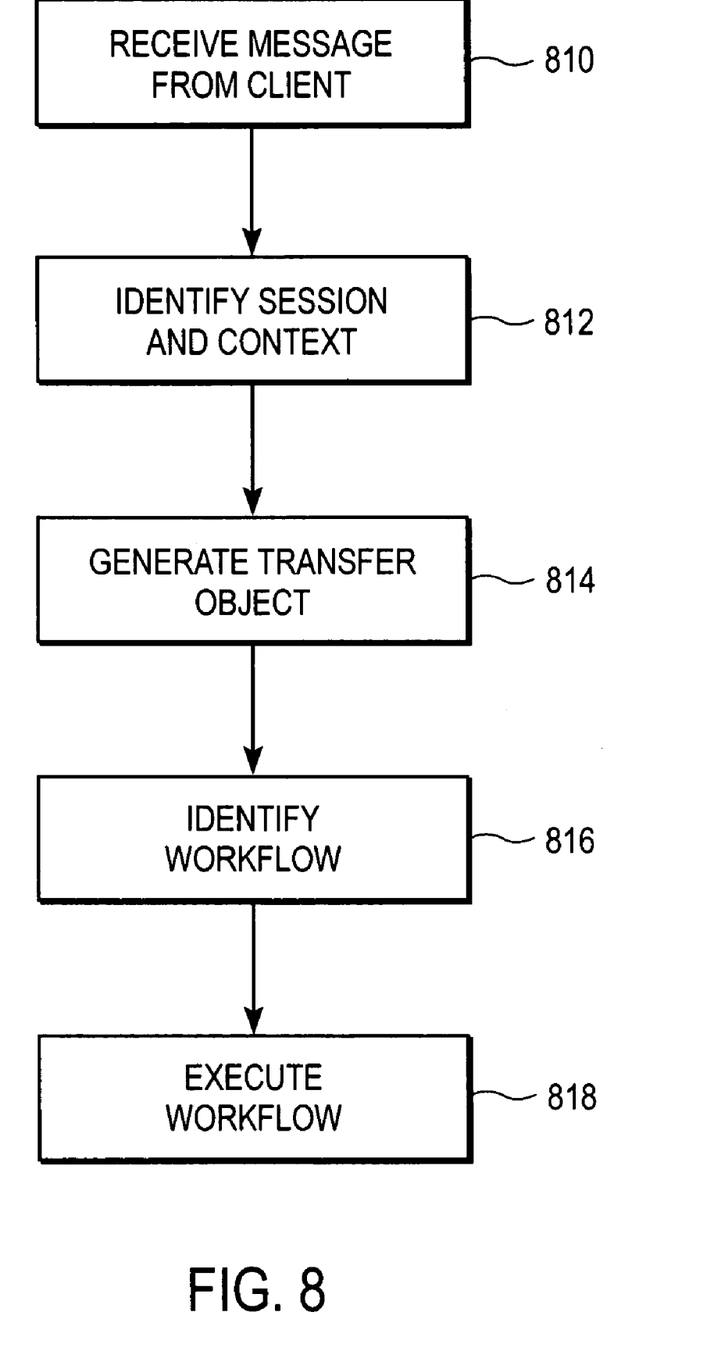
FIG. 8 illustrates steps performed by the information system to process a message received from a client.
Figure 9:
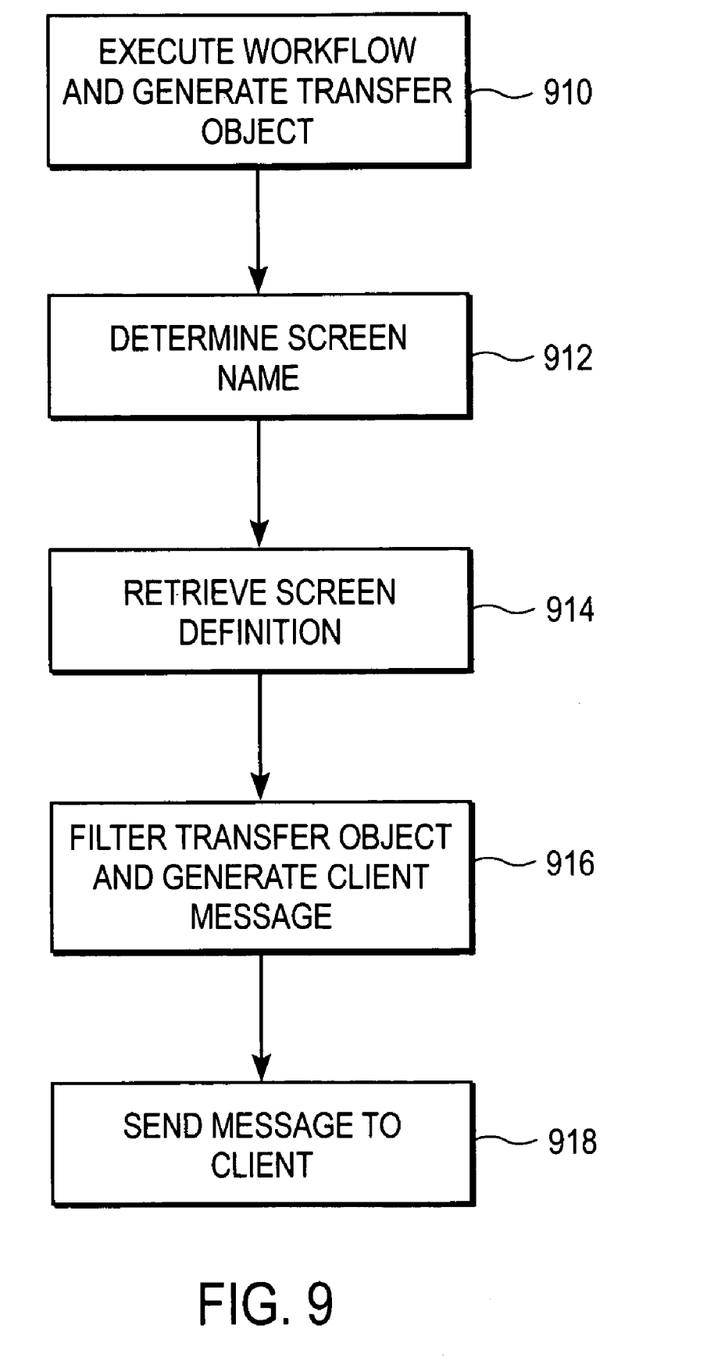
FIG. 9 illustrates steps performed by the information system to deliver a message to a client during processing of a workflow.

FIGS. 8 and 9 are flow charts illustrating steps performed by an embodiment of the IS 110 to execute a workflow. Other embodiments of the IS 110 perform the steps in different orders. Moreover, other embodiments perform different steps in addition to, or instead of, the ones described herein.

FIG. 8 illustrates steps performed by the IS 110 to process a message received from a client 112. Initially, the web server 116 receives 810 the message from the client 112. The message indicates an action that was performed by the end-user via a UI presented at the client, such as the selection of a patient or clicking an "OK" button. The web server 116 passes the message to the session support module 312. This module 312 identifies 812 the session to which the message belongs and also associates a context object with the message.

The transformation module 314 receives the message from the client 112 and generates 814 a transfer object encapsulating the information in the message. The application controller 316 receives the transfer and context objects and passes the objects to the workflow engine 213. The workflow engine 213 identifies the current point in the applicable workflow and executes the associated actions using the information in the transfer and/or context objects.

FIG. 9 illustrates steps performed by the IS 110 to deliver a message to a client 112 during processing of a workflow. The workflow engine 213 executes actions in the workflow and either generate a new transfer object or alters an existing transfer object as a result. In addition, the workflow engine 213 updates the context object to reflect that the engine executed a portion of the workflow.

The application controller 316 receives the transfer and context objects from the workflow engine 213. The application controller 316 supplies the context object to the view manager 318, and the view manager 318 uses the context to determine 912 the screen name for the current point in the process flow for the given session. In one embodiment, the view manager 318 stores the screen name in the context object.

The application control provides the transfer and context objects to the transformation module 314. The transformation module 314 uses the screen name to retrieve 914 the applicable screen definition for the session. The screen definition describes the UI elements to present at the client 112 and the data that are utilized by the UI elements. The transformation module 314 filters 916 the transfer object and/or the data in the IS 110 and generates a message for the client 112 that contains only the data utilized by the UI elements in the screen definition. The session support module 312 saves the context object, and the web server 116 sends 918 the message to the client 112.

The above description is included to illustrate the operation of the preferred embodiments and is not meant to limit the scope of the invention. The scope of the invention is to be limited only by the following claims. From the above discussion, many variations will be apparent to one skilled in the relevant art that would yet be encompassed by the spirit and scope of the invention.

We claim:

1. A computerized system for engaging in a communications session with a client to process a workflow, comprising:
   a screen definition module for identifying a screen definition defining a user interface for the client, the user interface presenting information at the client;
   a filtering module for filtering a set of information related to the workflow to obtain a subset containing the information presented at the client by the user interface defined by the screen definition; and
   a module for providing the screen definition and the subset of information to the client, wherein the client uses the screen definition to perform an activity based on the subset of information.

2. The system of claim 1, further comprising:
   a conversion module for converting the screen definition and the subset of information from an internal representation into a format utilized by the client.

3. The system of claim 1, further comprising:
   a database storing a plurality of screen definitions defining user interfaces for the client; and
   a context module for identifying a context for the communications session with the client;
   wherein the screen definition identified by the screen definition module is selected from the database responsive to the context.

4. The system of claim 3, wherein the context specifies a current point in a workflow being performed during the communications session, wherein there are a plurality of screen definitions applicable for the current point in the workflow, and wherein the screen definition identified by the screen definition module is selected responsive to the context.

5. The system of claim 4, wherein the context identifies a type of client device being utilized for the communications session and wherein the screen definition identified by the screen definition module is selected from the database responsive to the type of client device.

6. The system of claim 4, wherein the context identifies a role of an end-user utilizing the client for the communication session and wherein the screen definition identified by the screen definition module is selected from the database responsive to the end-user role.

7. A computerized system for engaging in a communications session with a client to process a workflow, comprising:
   a context module for providing a context for the communications session;
   a workflow engine for receiving the context, processing at least a portion of the workflow responsive to the context, and generating output data responsive thereto;
   a screen definition module for receiving the context and for identifying a screen definition defining a user interface for the client responsive to the context and the workflow, the user interface utilizing a subset of the output data;
   a filtering module for filtering the output data responsive to the identified screen definition to produce the subset of the output data utilized by the user interface; and
   a module for providing the screen definition and the subset of the output data to the client, wherein the client uses the screen definition to perform an activity based on the subset of the output data.

8. A computerized system for engaging in a communications session with a client to process a workflow, comprising:
   a screen definition module for identifying a screen definition defining a user interface for the client, the user interface presenting information at the client;
   a filtering module for filtering a set of information related to the workflow to obtain a subset containing the information presented at the client by the user interface defined by the screen definition; and a module for providing the screen definition and the subset of information to the client; wherein the client using the screen definition to perform and activity based on the subset of information.

9. The system of claim 7, wherein there are a plurality of workflows that can be performed by the workflow engine and wherein the workflow engine comprises:
   a workflow controller for selecting the workflow from among the plurality of workflows responsive to the context.

10. The system of claim 7, wherein the workflow engine comprises:
    an activity delegate for identifying one or more activities within the workflow that are ready for processing by the workflow engine, wherein the workflow engine processes the identified one or more activities.

11. The system of claim 7, wherein the workflow comprises a plurality of activities, and wherein the workflow engine comprises:
    a transition delegate for evaluating a result of an activity in the workflow processed by the workflow engine and identifying one or more subsequent activities in the workflow to process.

12. The system of claim 7, wherein the context specifies a current point in the workflow, wherein there are a plurality of screen definitions applicable for the current point in the workflow, and wherein the screen definition module identifies a screen definition selected from among the plurality of screen definitions responsive to the context.

13. The system of claim 7, wherein there are a plurality of screen definitions applicable for the workflow, wherein the context identifies a type of client device being utilized for the communications session, and wherein the screen definition module identifies a screen definition selected from among the plurality of screen definitions responsive to the type of client device.

14. The system of claim 7, wherein there are a plurality of screen definitions applicable for the work flow, wherein the context identifies a role of an end-user utilizing the client for the communications session, and wherein the screen definition module identifies a screen definition selected from among the plurality of screen definitions responsive to the end-user role.

15. A method of engaging in a communications session with a client to process a workflow, comprising:
processing at least a portion of the workflow and generating output data responsive thereto;
identifying a screen definition defining a user interface for the client responsive to a context for the communications session and the workflow, the user interface utilizing a subset of the output data;
filtering the output data responsive to the identified screen definition to produce the subset of the output data utilized by the identified screen definition; and
providing the screen definition and the subset of the output data to the client, wherein the client uses the screen definition to perform an activity based on the subset of the output data.

16. The method of claim 15, wherein there are a plurality of workflows that can be processed and further comprising:
selecting the workflow to be processed from among the plurality of workflows responsive to the context.

17. The method of claim 15, wherein processing at least a portion of the workflow comprises:
identifying, responsive to the context, one or more activities within the workflow that are ready for processing.

18. The method of claim 15, wherein the workflow comprises a plurality of activities and wherein processing at least a portion of the workflow comprises:
evaluating a result of a processed activity and identifying one or more subsequent activities in the workflow to process.

19. The method of claim 15, wherein the context specifies a current point in the workflow, wherein there are a plurality of screen definitions applicable for the current point in the workflow, and wherein the identifying comprises:
selecting from among the plurality of screen definitions responsive to the context.

20. The method of claim 19, wherein the context further specifies a type of client device being utilized for the communications session, and wherein the identifying comprises:
selecting from among the plurality of screen definitions responsive to the type of client device.

21. The method of claim 19, wherein the context further specifies a role of an end-user utilizing the client for the communications session, and wherein the identifying comprises:
selecting from among the plurality of screen definitions responsive to the user role.

22. A computer program product comprising:
a computer-readable medium having computer program logic embodied therein for engaging in a communications session with a client to process a workflow, the computer program logic comprising:
a workflow engine for processing at least a portion of the workflow and generating output data responsive thereto;
a screen definition module for identifying a screen definition defining a user interface for the client responsive to a context for the communications session and the workflow, the user interface utilizing a subset of the output data;
a filtering module for filtering the output data responsive to the identified screen definition to produce the subset of the output data utilized by the identified screen definition; and
a module providing the screen definition and the subset of the output data to the client.

23. The computer program product of 22, wherein there are a plurality of workflows that can be processed and wherein the workflow engine comprises:
a workflow controller for selecting the workflow to be processed from among the plurality of workflows responsive to the context.

24. The computer program product of claim 22, wherein the workflow engine comprises:
an activity delegate for identifying, responsive to the context, one or more activities within the workflow that are ready for processing.

25. The computer program product of claim 22, wherein the workflow engine comprises:
a transition delegate for evaluating a result of a processed activity and identifying one or more subsequent activities in the workflow to process.

26. The computer program product of claim 22, wherein the context specifies a current point in the workflow, wherein there are a plurality of screen definitions applicable for the current point in the workflow, and wherein the screen definition module selects from among the plurality of screen definitions responsive to the context.

27. The computer program product of claim 26, wherein the context further specifies a type of client device being utilized for the communications session, and wherein the screen definition module selects from among the plurality of screen definitions responsive to the type of client device.

28. The computer program product of claim 26, wherein the context further specifies a role of an end-user utilizing the client for the communications session, and wherein the screen definition module selects from among the plurality of screen definitions responsive to the user role.

* * * * *